US011363978B2

(12) United States Patent
Yang et al.

(10) Patent No.: US 11,363,978 B2
(45) Date of Patent: Jun. 21, 2022

(54) BLADDER MONITORING SYSTEM

(71) Applicant: Verathon Inc., Bothell, WA (US)

(72) Inventors: Fuxing Yang, Bothell, WA (US); Joon Hwan Choi, Bothell, WA (US); Si Luo, Bothell, WA (US); Dave Scott, Bothell, WA (US); Kendall R. Waters, Issaquah, WA (US)

(73) Assignee: Verathon Inc., Bothell, WA (US)

( * ) Notice: Subject to any disclaimer, the term of this patent is extended or adjusted under 35 U.S.C. 154(b) by 553 days.

(21) Appl. No.: 16/410,169

(22) Filed: May 13, 2019

(65) Prior Publication Data

US 2019/0357836 A1 Nov. 28, 2019

Related U.S. Application Data

(60) Provisional application No. 62/675,863, filed on May 24, 2018.

(51) Int. Cl.
*A61B 5/20* (2006.01)
*A61B 5/00* (2006.01)
(Continued)

(52) U.S. Cl.
CPC ............ *A61B 5/204* (2013.01); *A61B 5/0075* (2013.01); *A61B 5/0537* (2013.01); *A61B 5/6833* (2013.01); *A61B 8/085* (2013.01); *A61B 8/4455* (2013.01); *A61B 8/467* (2013.01); *A61B 8/56* (2013.01); *A61B 2503/06* (2013.01);
(Continued)

(58) Field of Classification Search
CPC ........ A61B 2503/06; A61B 2562/0219; A61B 2562/0271; A61B 2562/029; A61B 5/0002; A61B 5/0075; A61B 5/01; A61B 5/024; A61B 5/053; A61B 5/0537; A61B 5/0816; A61B 5/1112; A61B 5/1117; A61B 5/1118; A61B 5/204; A61B 5/318; A61B 5/6804; A61B 5/6823; A61B 5/6833; A61B 8/085; A61B 8/4227; A61B 8/4236;
(Continued)

(56) References Cited

U.S. PATENT DOCUMENTS 4,926,871 A   5/1990   Ganguly et al.
5,058,591 A   10/1991  Companion et al.
(Continued)

FOREIGN PATENT DOCUMENTS

WO   2016177901 A1   11/2016

OTHER PUBLICATIONS

International Search Report and Written Opinion issued in corresponding International Application No. PCT/US2019/031986, dated Sep. 2, 2019, 15 pages.

*Primary Examiner* — Mark D Remaly
(74) *Attorney, Agent, or Firm* — Snyder, Clark, Lesch & Chung, LLP

(57) ABSTRACT

A bladder monitoring system includes a scanning system and a wearable bladder monitoring device (or patch). The scanning system obtains scan data that shows a bladder in a patient and identifies, based on the scan data, a placement location on the patient for the wearable bladder monitoring device. The scanning system indicates the placement location to a user; and identifies customization settings for one or more sensors of the wearable bladder monitoring device to enable the one or more sensors to detect extents of the bladder when the wearable bladder monitoring device is attached at the placement location.

20 Claims, 13 Drawing Sheets

(51) Int. Cl.
  *A61B 5/0537* (2021.01)
  *A61B 8/08* (2006.01)
  *A61B 8/00* (2006.01)
(52) U.S. Cl.
  CPC . *A61B 2562/029* (2013.01); *A61B 2562/0219* (2013.01); *A61B 2562/0271* (2013.01)
(58) Field of Classification Search
  CPC ....... A61B 8/4455; A61B 8/467; A61B 8/483; A61B 8/56; A61B 8/585; G06K 2209/051
  See application file for complete search history.

(56) References Cited

U.S. PATENT DOCUMENTS

| | | |
|---|---|---|
| 5,416,469 A | 5/1995 | Colling |
| 5,423,329 A | 6/1995 | Ergas |
| 5,964,710 A | 10/1999 | Ganguly et al. |
| 6,149,636 A | 11/2000 | Roe et al. |
| 6,186,991 B1 | 2/2001 | Roe et al. |
| 6,213,949 B1 | 4/2001 | Ganguly et al. |
| 6,238,344 B1 | 5/2001 | Gamelsky et al. |
| 6,266,557 B1 | 7/2001 | Roe et al. |
| 6,359,190 B1 | 3/2002 | Ter-Ovanesyan et al. |
| 6,406,431 B1 | 6/2002 | Barnard et al. |
| 6,565,512 B1 | 5/2003 | Ganguly et al. |
| 6,911,912 B2 | 6/2005 | Roe |
| 6,970,091 B2 | 11/2005 | Roe |
| 7,749,165 B2 | 7/2010 | McMorrow et al. |
| 8,072,338 B2 | 12/2011 | Rondoni et al. |
| 8,221,321 B2 | 7/2012 | McMorrow et al. |
| 8,308,644 B2 | 11/2012 | McMorrow et al. |
| 8,805,508 B2 | 8/2014 | Gerber et al. |
| 2006/0079775 A1 | 4/2006 | McMorrow et al. |
| 2007/0004938 A1 | 1/2007 | Guerra |
| 2016/0058412 A1 | 3/2016 | Yoshimura et al. |
| 2017/0258386 A1 | 9/2017 | Woltjer et al. |

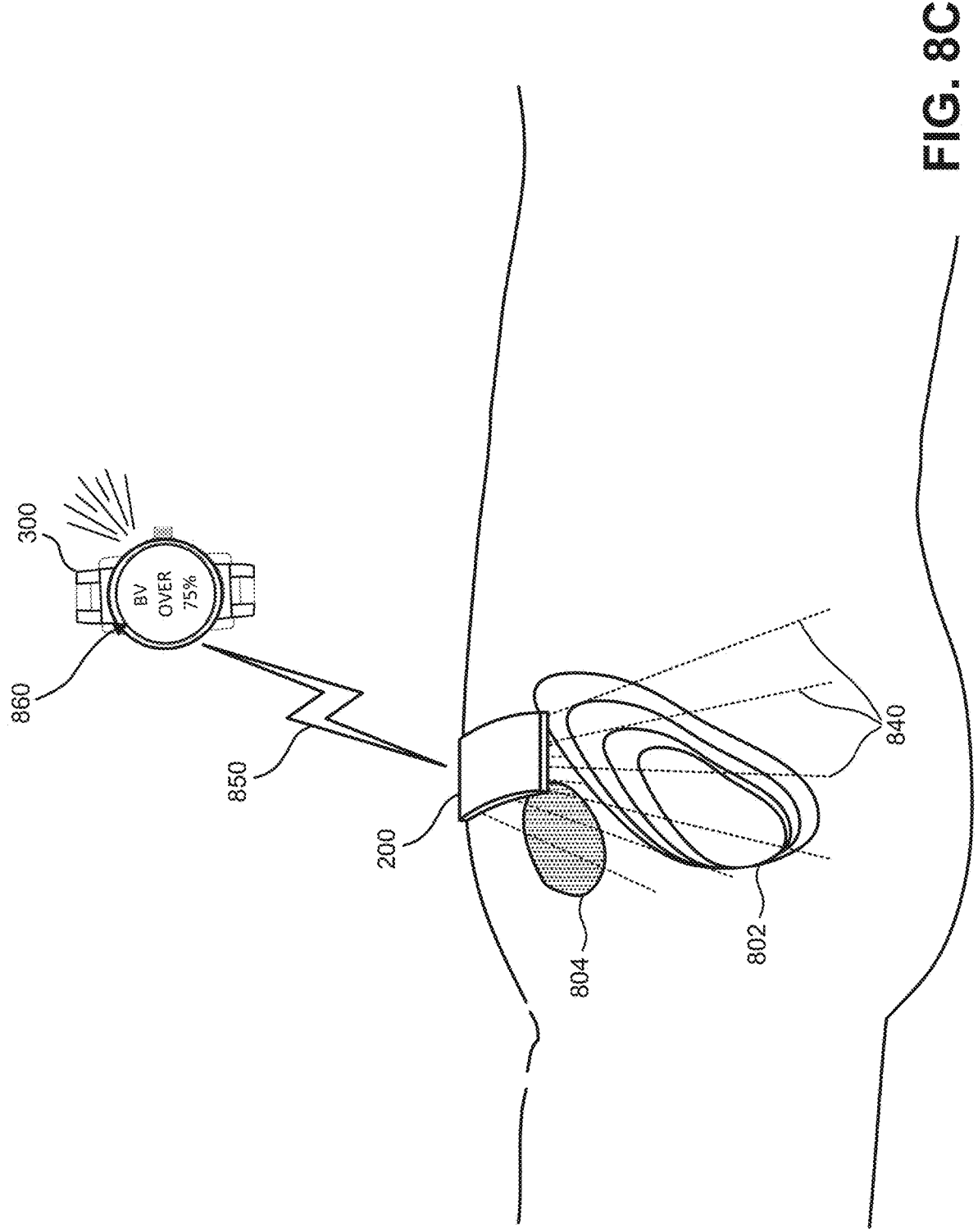

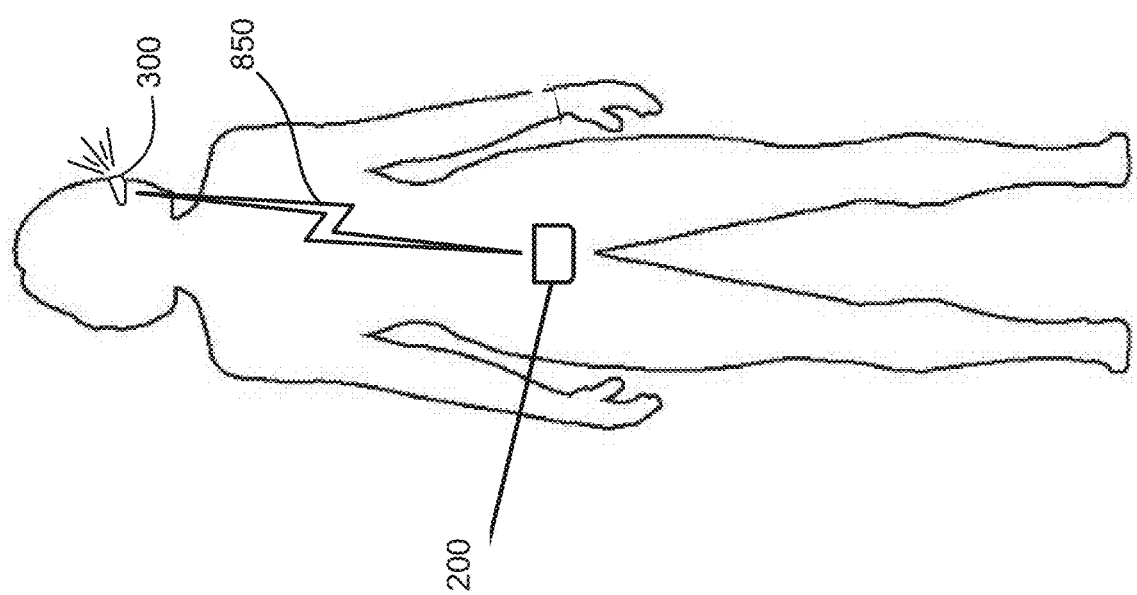

BLADDER MONITORING SYSTEM

CROSS-REFERENCE TO RELATED APPLICATION

This application claims priority under 35 U.S.C. § 119, based on U.S. Provisional Patent Application No. 62/675,863 filed May 24, 2018, the disclosure of which is hereby incorporated by reference.

BACKGROUND OF THE INVENTION

Loss of the sensation of bladder fullness is a common clinical problem often seen in patients suffering from spinal cord injury, stroke aftermath, and diabetes mellitus; additionally, a lack of understanding of the sensation is found in some people with intellectual disabilities. The problem is often accompanied by urinary incontinence, which is not only lifestyle-limiting but can be a serious health problem when retention causes urine backup into the kidneys and induces infection.

BRIEF DESCRIPTION OF THE DRAWINGS

FIGS. 8A-8C are simplified schematics of customization and notification procedures using the bladder monitoring system described herein;

FIG. 11 is a simplified schematic of a portion of the bladder monitoring system, according to another implementation described herein.

DETAILED DESCRIPTION OF THE PREFERRED EMBODIMENTS

Figure 1:
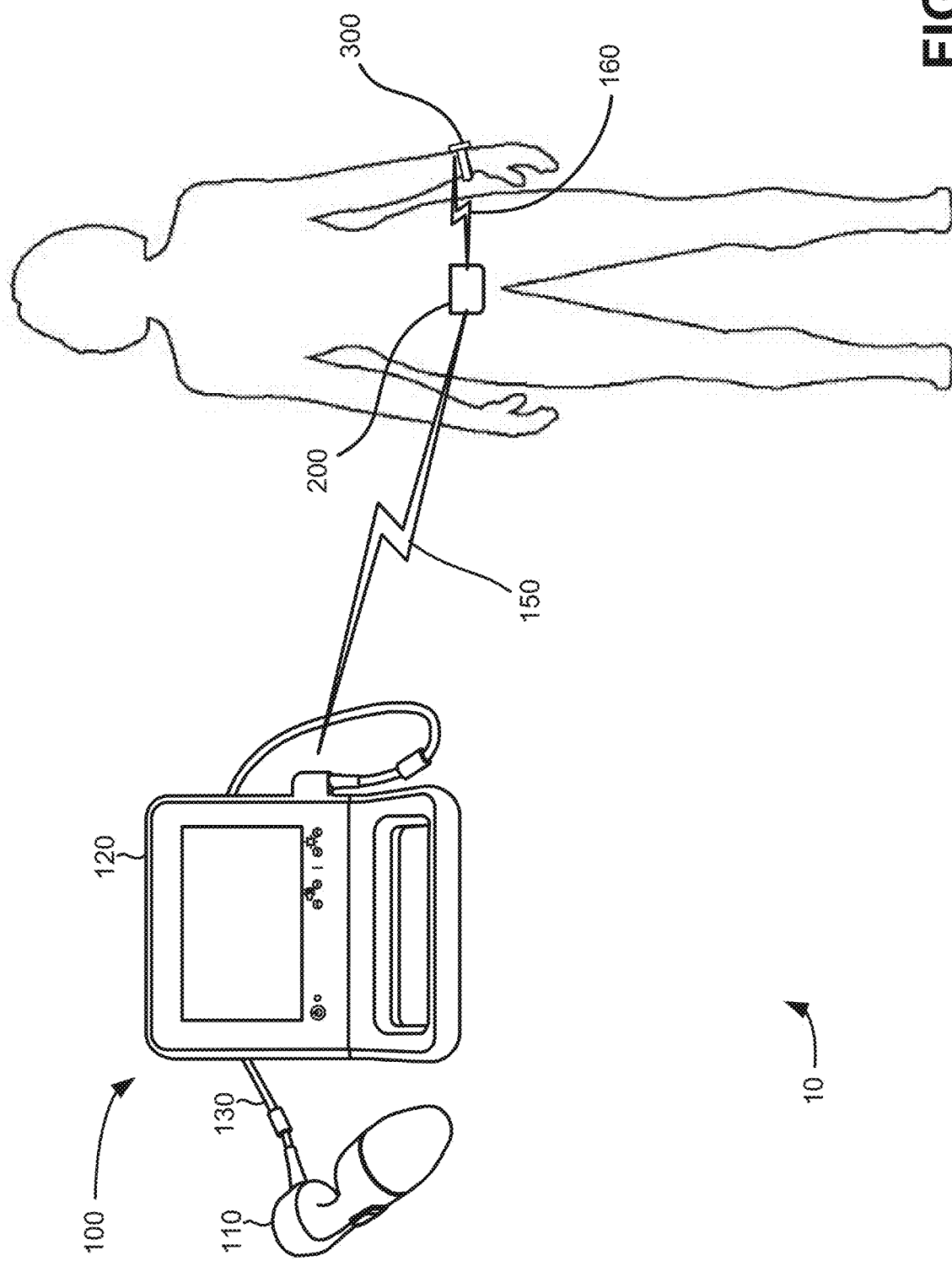
FIG. 1 is a schematic of a bladder monitoring system in which systems and methods described herein may be implemented.

The following detailed description refers to the accompanying drawings. The same reference numbers in different drawings may identify the same or similar elements.

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. In some implementations, the ultrasound probe may perform scans in multiple planes to generate a volume scan (e.g., for a bladder). The ultrasound probe can provide accurate results, but generally requires operation by a technician.

Bladder monitoring systems that continuously record and monitor bladder fullness can be used to alert the wearer (or a caretaker) when voiding is required. These systems may be worn by or attached to a patient to continuously detect bladder volume.

To achieve a wearable size, continuous bladder monitors typically use a patch that produces a limited number of acoustic beams (or other signals) to estimate a changing bladder volume. Due in part to this limited functionality and the variety of bodily dimensions among patients (e.g., human subjects), patch settings must be customized for each individual in conjunction with proper initial placement location to achieve optimal effectiveness. For example, body variations among children, males, females, obese/slender body types, etc., generally preclude use of patch settings that are universally suitable for all patients. Customization may include configuring the physical or logical properties of a patch to provide accurate measurements of an organ in a specific wearer's body. Customization settings for a patch may change physical properties, such as adjusting steering angles and beam intensities of sensors in the patch, and/or logical properties, such as adjusting how raw sensor data from the patch is interpreted. This customization procedure is an important step to achieve accurate monitoring for each individual. In some cases, the customization settings can be combined with a physician's prescription, if any, to ensure repeatable performance for replacement patches without having to repeat the customization procedure at each patch application.

Implementations described herein provide an advanced bladder monitoring system with guidance for patch placement and simplified patch customization procedures. Guidance by a bladder scanning system provides position and other customization settings before the patch is applied on a patient. This pre-placement scanning step simplifies the customization procedure and improves the patch's fullness monitoring precision. In one implementation, the bladder scanning system can provide information such as bladder shape under specific volume, depth under specific volume, width under specific volume, related position to the pubic bone (e.g., pubic synthesis), etc. This information can be used to determine optimal patch placement locations/orientations for a patient and patch customization settings that ensure accurate bladder measurements. After patch placement, bladder scan data may also be combined with sensor reading from the patch to calibrate bladder sensor readings with predicted bladder volumes. In some embodiments, after an initial customization process, a set of multiple patches with identical configurations can be provided to a patient for disposable use (e.g., outside the confines of a medical facility). In other embodiments, patch 200 may be include certain disposable components (e.g., a two-sided adhesive, an adhesive frame, etc.,) that permit removal and re-attachment of patch 200 to the patient.

According to one implementation, a bladder monitoring system includes a scanning system, a monitoring patch, and a notification device. The scanning system includes an ultrasound probe, a processing unit, and a first communication interface. The monitoring patch includes one or more sensors to detect fluid in a bladder of a patient and a second communication interface to communicate with the scanning system and the notification device. The monitoring patch includes a wearable device configured to be attached to the patient. The notification device includes a third communication interface to receive monitoring signals from the monitoring patch. The scanning system identifies the bladder using scan data from the ultrasound probe, and indicates to a user, based on the scan data, a location on the patient where the monitoring patch should be attached. Additionally, or alternatively, the scanning system may provide customization settings for the one or more sensors in the monitoring patch. The customization settings may be based on the scan data, a default patch sensor configuration, and/or reference signals received from the attached patch.

FIG. 1 provides a simplified schematic of bladder monitoring system 10 in which systems and methods described herein may be implemented. As shown in FIG. 1, bladder monitoring system 10 may include a scanning system 100, a bladder monitoring patch 200, and a notification device 300.

Scanning system 100 may include an ultrasound bladder scanner and additional hardware/software for connectivity to the other components in monitoring system 10. Scanning system 100 may receive and process echo data to generate three-dimensional (3D) image data that can be used to determine the location and extents of an organ, such as bladder size and/or volume. Scanning system 100 includes a probe 110, a base unit 120, and a cable 130. In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

Probe 110 includes a handle portion, a trigger, and a nose (or dome) portion. Medical personnel may hold probe 110 via the handle and press the trigger to activate one or more ultrasound transceivers, located in the nose portion, to transmit ultrasound signals toward a target organ of interest on a patient. The dome of probe 110 is typically formed of a material that provides an appropriate acoustical impedance match to an anatomical portion and/or permits ultrasound energy to be properly focused as it is projected into the anatomical portion.

Probe 110 includes one or more ultrasound transceiver elements and one or more transducer elements (not visible in FIG. 1) within the dome that transmit ultrasound energy outwardly from the dome, and receive acoustic reflections or echoes generated by internal structures/tissue within the anatomical portion. For example, the one or more ultrasound transducer elements may include a one-dimensional, or a two-dimensional array of piezoelectric or capacitive elements that may be moved within the dome by a motor to provide different scan directions with respect to the transmission of ultrasound signals by the transceiver elements. Alternatively, the transducer elements may be stationary with respect to probe 110 so that the selected anatomical region may be scanned by selectively energizing the elements in the array. Probe 110 may communicate with base unit 120 via a wired connection, such as via cable 130. In other implementations, probe 110 may communicate with base unit 120 via a short-range wireless connection (e.g., Bluetooth®, Wi-Fi®, etc.).

Base unit 120 may process ultrasound echoes provided by probe 110 to detect an organ (e.g., a bladder) and determine the organ location, dimensions, volume, etc. Base unit 120 includes a display to allow a user to view processed results from an ultrasound scan, and/or to allow operational interaction with respect to the user during operation of probe 110. For example, the display of base unit 120 may provide instructions for positioning probe 110 and bladder monitoring patch 200 relative to the selected anatomical portion of the patient. The display may also display two-dimensional or three-dimensional images of the selected anatomical region.

Bladder monitoring patch 200 (also referred to as a "wearable bladder monitoring device," or simply as "patch 200") may be attached to a patient using an adhesive, embedding in a garment, integrating with a belt, or another positioning mechanism. Generally, patch 200 may provide a wearable form factor to continuously monitor bladder volume. Patch 200 may include one or more sensors to detect bladder fullness. For example, different sensors in patch 200 may scan along different lines and may register a positive reading when urine is detected. Sensors for patch 200 may include ultrasound sensors, bio-impedance sensors, bio-reactance sensors, radio frequency (RF) sensors, infrared sensors, or the like. In contrast with scanning system 100, patch 200 may provide a small number of sensing beams (e.g., acoustic beams, etc.) to identify different fluid levels in a bladder. In one implementation, sensors in patch 200 may be provided with a default configuration that can be adjusted or customized. Patch 200 may exchange information with scanning system 100 to provide customized sensor adjustments for a particular application on a patient. According to one implementation, sensors in patch 200 may be programmed to adjust the characteristics of RF signals, such as the carrier frequency, acoustic intensity, steering angel (for array transducer), pulse repeating frequency (PRF), signal bias, gain level, pre-processing method, etc., in achieving the optimal performance for each individual patient. Additionally, patch 200 may transmit sensor readings and/or alert signals to notification device 300.

According to another implementation, patch 200 may be included within a multipurpose healthcare device. For example, patch 200 may include other wearable bio sensor technology such as an inertial measurement unit, ECG/infrared sensor, microphone, temperature, humidity, etc. Additionally, or alternatively, patch 200 may include Global Position System (GPS) or RFID technology. Thus, in some implementations, patch 200 may provide useful health information such as heart rate, respiratory rate, activity, posture, fall indications, etc., as well as bladder volume.

Scanning system 100 and patch 200 may include a communication interface 150, such as a Wi-Fi® interface, a Bluetooth® wireless interface, a radio-frequency identification (RFID) interface, a near-field communications (NFC) wireless interface, an infra-red (IR) communications interface, and/or any other type of short-range wireless interface to exchange data. Additionally or alternatively, scanning system 100 and patch 200 may be connected via a physical connection, such as a universal serial bus (USB) or a Lightning® cable. In one implementation, scanning system 100 may receive sensor readings from patch 200 during an initial configuration period and provide customization instructions to patch 200. In one implementation, customization instructions may correlate particular combinations of sensor readings from patch 200 with corresponding bladder volume levels (e.g., based on the sensor readings and scan data from scanning system 100). In another implementation described further herein, customization data may include additional instructions for tuning sensors in patch 200. In another configuration, scanning system 100 and patch 200 may exchange information indirectly through notification device 300 (e.g., notification device 300 may have a wired or wireless connection with both scanning system 100 and patch 200). According to one implementation, patch 200 may be a disposable component, where a set of multiple patches 200 may be configured with the same customization instructions for disposable use by a specific patient.

Notification device 300 may include a device to process signals transmitted from patch 200 and provide audible, visible, or tactile notifications to a patient. In one implementation, notification device 300 may include a dedicated device for receiving signals from patch 200 and generating alert signals to a patient or caretaker. For example, notification device 300 may include an earpiece, lanyard, or lapel brooch with a direct connection (e.g., wired or wireless) to patch 200. In another implementation, notification device 300 may include a general purpose wearable computing device equipped with an application to process signals transmitted from patch 200 and/or scanning system 100. For example, notification device 300 may include a smart watch, or a computer pendant. In still another implementation, notification device 300 may include a smart phone, tablet, or another portable computing or communication device.

Notification device 300 and patch 200 may further include a short-range wireless networking interface 160, such as a Bluetooth® wireless interface, an RFID interface, an NFC wireless interface, an IR communications interface, and/or any other type of interface to exchange data. Additionally or alternatively, notification device 300 and patch 200 may be connected via a physical connection, such as a universal serial bus (USB) or a Lightning® cable. In one implementation, notification device 300 may receive alert signals from patch 200, when patch 200 determines that a bladder volume alert level for a patient has been reached. In another implementation, notification device 300 may analyze and integrate the information from a single patch 200 or multiple patches 200 and make a decision of whether an alert should be triggered.

Although FIG. 1 shows exemplary components of bladder monitoring system 10, in other implementations, bladder monitoring system 10 may include fewer components, different components, additional components, or differently-arranged components than depicted in FIG. 1. Additionally or alternatively, one or more components of bladder monitoring system 10 may perform one or more tasks described as being performed by one or more other components of bladder monitoring system 10. For example, in another implementation, probe 110 and base unit 120 may be combined in a single component. In another example, one or more functions of notification device 300 may be performed by patch 200.

Figure 2:
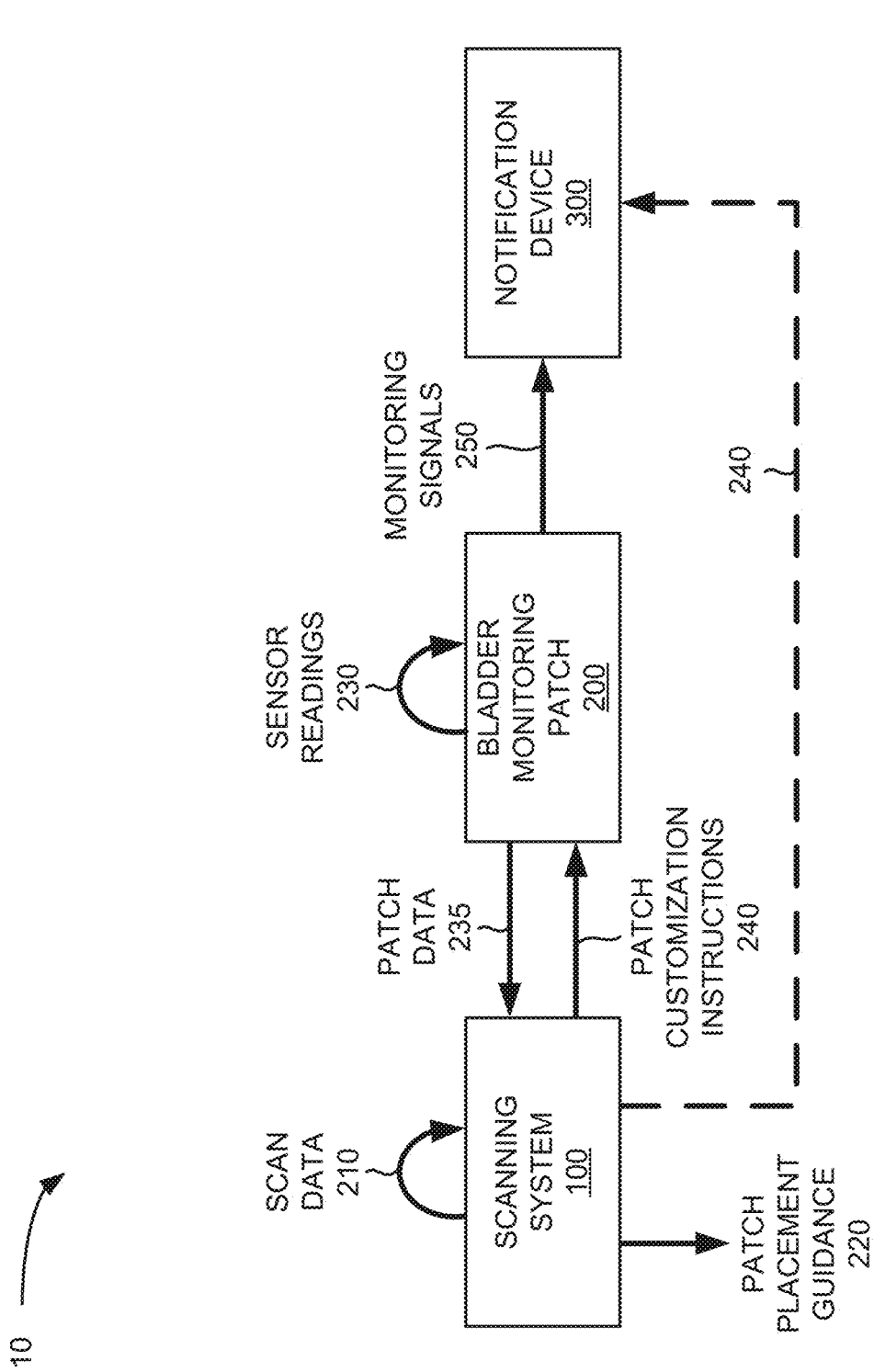
FIG. 2 is a block diagram illustrating exemplary communications among components of the bladder monitoring system of FIG. 1.

FIG. 2 is a block diagram showing exemplary communications among components of bladder monitoring system 10. As shown in FIG. 1, scanning system 100 may acquire scan data 210. For example, probe 110 may include a transceiver that produces ultrasound signals, receives echoes from the transmitted signals and generates B-mode image data based on the received echoes. Scanning system 100 may include, for example, demodulation, decimation, log compression, and filtering sub-modules, to generate an image that can be presented for visualization by a technician (e.g., a person). A rotating transducer or transducer array within probe 110 may scan along multiple scan planes. Echo data may be processed to generate 3D image data that can be used to determine bladder size and/or volume. Post-processing logic in scanning system 100 may provide additional analysis of scan data 210, such as cavity-type recognition, volume estimations, or other clinically useful information. For example, scanning system 100 may identify a cavity as a bladder and/or estimate a volume for the bladder. Additionally, scanning system 100 may identify a pubic bone shadow, bladder aiming/clipping information, or other artifacts that impact placement of patch 200.

Based on processing of scan data 210, scanning system 100 may identify an optimal placement location/orientation for patch 200. In one implementation, scanning system 100 may output patch placement guidance 220 as a visual indication or overlay on a display portion of base 120. In another implementation, scanning system 100 may provide a visual or audible signal when probe 110 is in a position on the patient that corresponds to the optimal location for patch 200. The optimal location may, for example, minimize pubic bone interference and capture desired extents of a bladder with different fluid volumes. For example, patch placement guidance 220 may include an audible signal or textual message to hold probe 110 stationary when probe 110 is located over a portion of the skin that corresponds to an optimal patch 200 location. Patch placement guidance 220 allows a technician to apply patch 200 at the location of probe 110 or to mark the location on the patient's skin where patch 200 is to be applied later. In other implementations, patch placement guidance 200 may include another type of instructions for identifying the patch location, such as a generating a schematic of the patient with the patch location and orientation being indicated or combining scan information with an image of the patient's abdominal region to provide an augmented reality placement system (e.g., that can be used with notification device 300 to indicate a patch placement location and orientation).

Patch 200 may be applied to the patient (at the indicted optimal location) and activated to collect sensor readings 230. Patch 200 may forward sensor readings 230 and other patch configuration information (e.g., patch type, number of sensors, etc.) to scanning system 100 as patch data 235 (also referred to herein as reference signals). Scanning system 100 may read patch data 235 and may calibrate particular sensor locations/readings with bladder volume levels. For example, as described further herein, scanning system 100 may associate positive readings from one or more sensor combinations with a different bladder volume percentage (e.g., 25%, 55%, 80%, etc.) or volume amount (e.g., 100 cubic centimeters ($cm^3$), 150 $cm^3$, 300 $cm^3$, etc.).

In some implementations, where patch 200 is configurable, scanning system 100 may provide programming instructions to adjust characteristics of RF signals generated by patch 200 to achieve optimal performance for the individual patient. In one implementation, scanning system 100 may provide customization settings to patch 200 prior to attachment of patch 200 to the patient (e.g., based on scan data from probe 110 and default properties of patch 200). In another implementation, scanning system 100 may provide additional customization settings to patch 200 after patch 200 is applied to the patient, with the additional customization settings based on actual sensor feedback from patch 200 to fine-tune the patch sensors. Scanning system 100 may provide customization settings and programming instructions to patch 200 as patch customization instructions 240. In some implementations, multiple iterations of patch data 235 and patch customization instructions 240 may be used. In other implementations, customization instructions 240 may be output for use by a technician to manually program patch 200. Additionally, or alternatively, if patch 200 lacks the capability to implement/store customization instructions 240, scanning system 100 may forward customization instructions 240 to notification device 300.

Still referring to FIG. 2, patch 200 may begin monitoring bladder volume of the patient. In one implementation, patch 200 may receive patch customization instructions 240 and may generate monitoring signals 250 at periodic intervals or upon request from notification device 300. In another implementation, patch 200 may provide monitoring signals when an alarm state is identified (e.g., a particular volume level is reached). In still another implementation, patch 200 may provide periodic monitoring signals 250 that include raw sensor data (e.g., indicating one or more positive sensor readings) that may be interpreted by notification device 300 based on patch customization instructions 240.

Although FIG. 2 shows exemplary communications within bladder monitoring system 10, in other implementations, different communications may be used than depicted in FIG. 2. For example, in another implementation, patch data 235 and patch customization instructions 240 may be sent indirectly through an intermediate device (e.g., notification device 300).

Figure 3:
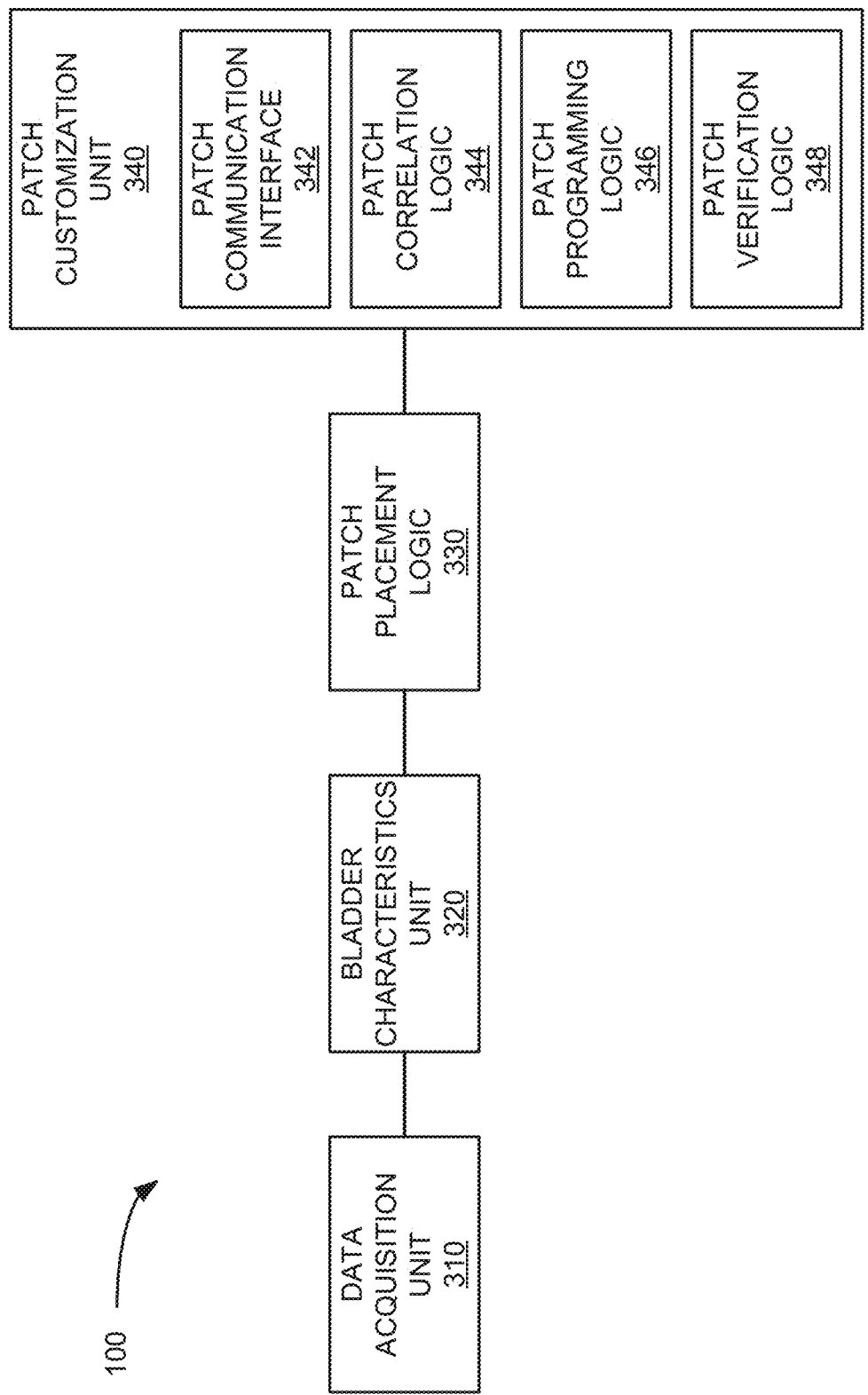
FIG. 3 is a block diagram of exemplary functional logic components implemented in the scanning system of FIG. 1.

FIG. 3 is a block diagram of functional logic components implemented in scanning system 100, in accordance with an exemplary implementation. Referring to FIG. 3, scanning system 100 includes a data acquisition unit 310, a bladder characteristics unit 320, patch placement logic 330, and a patch customization unit 340. In an exemplary implementation, data acquisition unit 310 may be part of probe 110 and the other functional units (e.g., bladder characteristics unit 320, patch placement logic 330, and a patch customization unit 340) may be implemented in base unit 120. In other implementations, the particular units and/or logic may be implemented by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., Wi-Fi®, Bluetooth®, or some other wireless protocol/technology) that is located remotely from probe 110 and base unit 120. Such an environment may facilitate efficient storage and dissemination of sensor data and/or alarm conditions to various entities, such as caregivers, healthcare providers, etc.

As described above, probe 110 may include a transceiver that produces ultrasound signals, receives echoes from the transmitted signals and generates B-mode image data based on the received echoes. In an exemplary implementation, data acquisition unit 310 obtains data associated with multiple scan planes corresponding to the region of interest (e.g., a bladder and surrounding area) in a patient. For example, probe 110 may receive echo data that is processed by data acquisition unit 310 to generate two-dimensional (2-D) B-mode image data to determine bladder size and/or volume. In other implementations, probe 110 may receive echo data that is processed to generate three-dimensional (3D) image data that can be used to determine bladder size and/or volume.

Bladder characteristics unit 320 may collect information on bladder volume and anatomical information around the patient's bladder. Bladder characteristics unit 320 may apply noise reduction, adjust the aspect ratio of the raw B-mode image, apply a scan conversion, and perform other data processing tasks to identify an organ (e.g., a bladder) of a patient. Bladder characteristics unit 320 may provide additional analysis of a defined organ, such as cavity-type recognition, volume estimations, width dimensions for a specific volume estimate, depth dimensions for a specific volume estimate, or other information about a bladder (e.g., bladder position relative to the probe, or other artifacts such as bladder clipping or pubic bone shadow).

Patch placement logic 330 may detect an optimal placement location for patch 200. In one implementation, a patch type, patch dimensions, patch characteristics, or other descriptive information about patch 200 may be provided to (and/or stored by) patch placement logic 330. For example, a model number, the number of sensors, and/or the dimensions of patch 200 may be provided to patch placement logic 300 by user input or via a wireless connection with patch 200 (such as patch communication interface 342, described below). Patch placement logic 330 may use these patch characteristics, along with information from bladder characteristics unit 320, to determine an optimal placement location for patch 200. An optimal location may include, for example, a location where sensors in patch 200 can have unobstructed access to all or a relevant portion of a patient's bladder and where the sensors can sense a volume change within the patient's bladder (e.g. along a complete bladder volume range or an upper bladder volume range). In one implementation, a designated location of probe 110 may correspond to the optimal location for patch 200. Thus, patch placement logic 330 may signal when probe 110 is in the appropriate location on the patient, so that a technician can mark the optimal patch location (or simply apply patch 200).

Patch customization unit 340 may communicate with patch 200 to calibrate patch sensor readings (e.g., reference signals) with estimated bladder volume values and to provide customization settings to adapt patch 200 to a specific patient. Patch customization unit 340 may include a patch communication interface 342, patch correlation logic 344, patch programming logic 346, and patch verification logic 348. Patch customization unit 340 may communicate with a single patch 200 or multiple monitoring patches and may receive data from each monitoring patch and integrate the information from the patches for systems using customization.

Patch communication interface 342 may provide a communication path between scanning system 100 and patch 200. Patch communication interface 342 may employ a wire or wireless network protocols. In one implementation, patch communication interface 342 may use proprietary application programming interface (API) calls to facilitate data transfers between patch 200 and scanning system 100.

Patch correlation logic 344 may receive sensor readings from patch 200 (e.g., after patch 200 is applied in the optimal location determined by patch placement logic 330) and match the sensor readings to volume levels for a patient's bladder. Patch correlation logic 344 may apply measured bladder characteristics from bladder characteristics unit 320 to correlate sensor echo directions to particular areas/sizes/volumes of the patient's bladder.

Patch programming logic 346 may program parameters for patch 200 to provide optimal sensing of bladder volumes. Patch programming logic 346 may program characteristics of RF signals, such as the carrier frequency, acoustic intensity, steering angel (for an array transducer), pulse repeating frequency (PRF), signal bias, gain level, pre-processing method, etc. Patch programming logic 346 may identify customization settings for patch 200 based on, for example, patient information (e.g., size, weight, gender, etc.) and bladder characteristics (e.g., from bladder characteristics unit 320). In one implementation, using patch communication interface 342, patch programming logic 346 may remotely adjust parameters of patch 200 to best cover dimensions of a patient's bladder.

Patch verification logic 348 may read data from monitoring patch(es) 200 and verify the accuracy of the bladder volume measurement data provided by the monitoring patches. For example, after initial placement of patch 200 and/or after customization by patch programming logic 346, patch verification logic 348 may receive additional signals from patch 200 to compare with measured bladder characteristics from bladder characteristics unit 320.

Although FIG. 3 shows exemplary logical components of scanning system 100, in other implementations, scanning system 100 may include fewer logical components, different logical components, or additional logical components than depicted in FIG. 3. Additionally or alternatively, functions of one or more logical components of scanning system 100 may be performed by one physical component or distributed across multiple physical components. In another implementation, one or more of the logical components of scanning system 100 may be performed in conjunction with another device, such as notification device 300. For example, one or more features of patch correlation logic 344, patch programming logic 346, or patch verification logic 348 may be performed by notification device 300 or performed by logic within patch 200.

Figure 4:
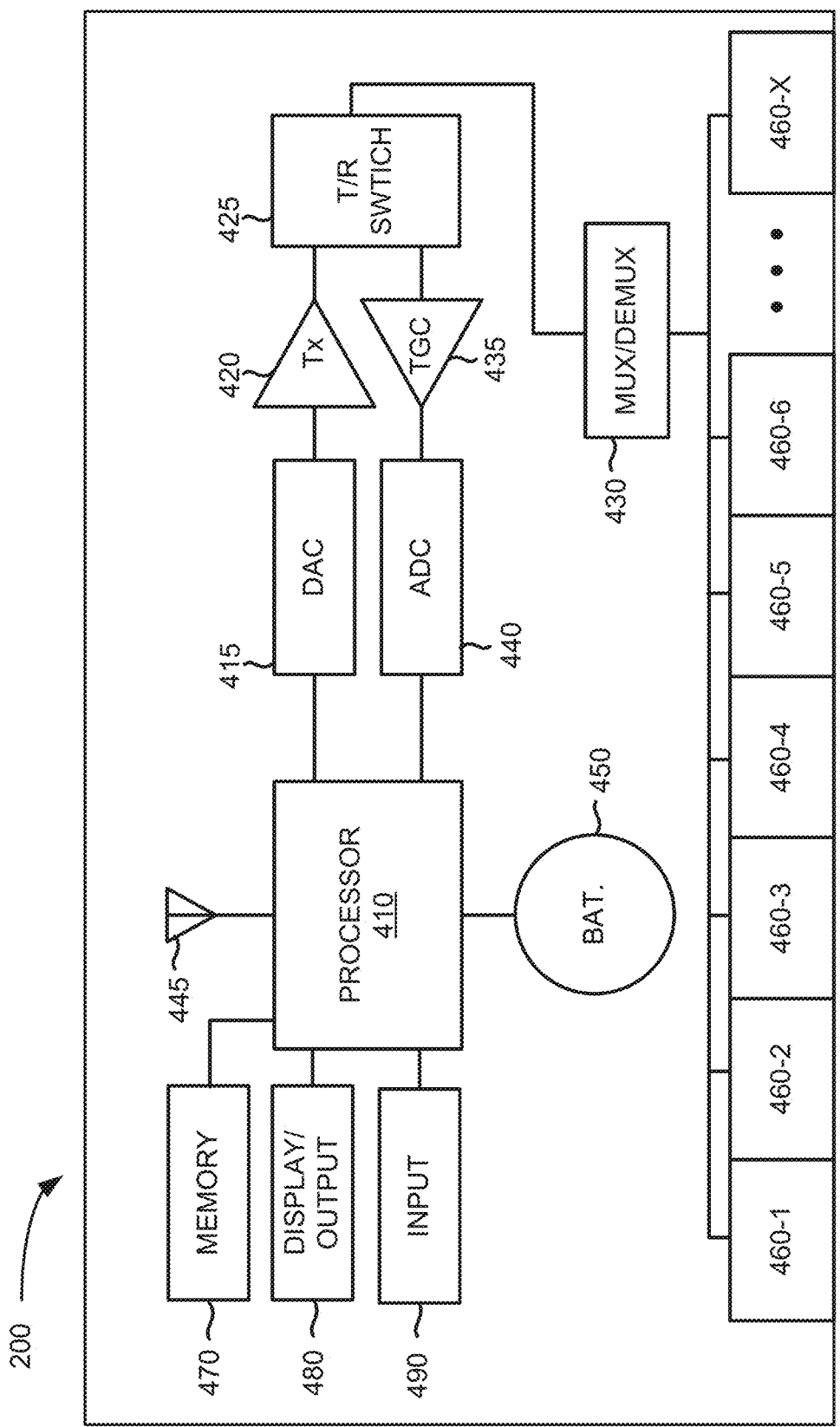
FIG. 4 is a diagram of exemplary components of the monitoring patch of FIG. 1.

FIG. 4 is a diagram of exemplary components of monitoring patch 200, in accordance with an exemplary implementation. In the example of FIG. 4, patch 200 may include an ultrasound sensing patch. Patch 200 may include a processor 410 (e.g., a field-programmable gate array (FPGA), ARM microcontroller, etc.), a digital-to-analog converter (DAC) 415, a transmitter (Tx) 420, a transmit/receive (T/R) switch 425, a multiplexer/demultiplexer (MUX/DEMUX) 430, time-gain compensation (TGC) circuitry 435, and an analog-to-digital converter (ADC) 440. Patch 200 may further include an antenna 445 to transmit and receive information, a battery 550 for power, and ultrasound transducers 460-1 through 460-X (collectively referred to as ultrasound transducers 460). Additionally, in some embodiments, patch 200 may include a memory 470, a display/output 480, and an input unit 490.

In one implementation, ultrasound transducers 460 may include an array of one or more transducer elements (e.g., 1, 4, 8, 12, 20, etc.). The transducer elements may be made of a piezoelectric material (e.g., PZT, PMN-PT), a piezocomposite material (e.g., PZT and polyurethane interstitial material), or a microelectromechanical system (MEMS) design (e.g., piezoelectric micro-machined ultrasound transducer or capacitive micro-machined ultrasound transducer). Processor 410 may control the transmit and receive sequence of ultrasound transducers 460, the processing of the received ultrasound signals, and the wireless transmission and reception of bladder-related information. As described above in connection with patch programming logic 346, for example, patch 200 may be programmed by scanning system 100 to adjust the characteristics of ultrasound transducers 460 and/or other aspects of patch 200. For example, a center frequency for ultrasound transducers 460 may be adjusted based on patient information (e.g., lower frequency for heavier patient); steering angles for ultrasound transducers 460 may be adjusted to modify a patch field of view based on patient dimensions (e.g., use a narrower field of view for smaller patient); or the rate of monitoring (or PRF) may be adjusted to account for different patient conditions (e.g., increase rate of monitoring depending on type of urinary incontinence).

Processor 410 may calculate bladder volume information based on signals received from ultrasound transducers 460. The calculated bladder volume information may include a quantitative bladder volume (e.g., reported in mL or CC) or a qualitative bladder volume (e.g., low, moderate, high, etc.). In one implementation, processor 410 may include logic to decide if an alert (e.g., for a full or nearly full bladder) should be issued and transmitted to notification device 300. In another implementation, processor 410 may provide bladder volume readings or raw signal data to notification device 300 for use in determining if an alert should be issued. In still another implementation, processor 410 may perform a periodic system check to confirm patch conditions, such as proper placement or adherence of patch 200 on the patient. For example, processor 410 may provide a warning signal if transducers 460 show an instantaneous drop-off or readings outside an expected range.

According to one implementation, memory 470 may store instructions, such as instructions used by processor 410 to customize patch 200 for a particular patient. Display/output 480 may include a component that outputs information to the user, such as a liquid crystal display (LCD) screen, a speaker, one or more light emitting diodes (LEDs), a vibration motor, etc.

Input unit 490 may include a mechanism that permits a user to input information to device patch 200, such as a keypad, a button, a switch, etc. In one implementation, input unit 490 may be combined with display/output unit 480 as a touch-sensitive display.

Although FIG. 4 shows exemplary components of patch 200, in other implementations, patch 200 may include fewer components, different logical components, or additional logical components than depicted in FIG. 4. Additionally, other sensor types and corresponding hardware/software may be used in patch 200. For example, in another implementation, patch 200 may use a near-infrared spectroscopy (NIRS) sensor to measure bladder volume by monitoring NIR light absorption due to water-based urine. In another example, patch 200 may include a bioelectrical impedance sensor to measure bladder volume by monitoring the electrical impedance of urine.

Figure 5:
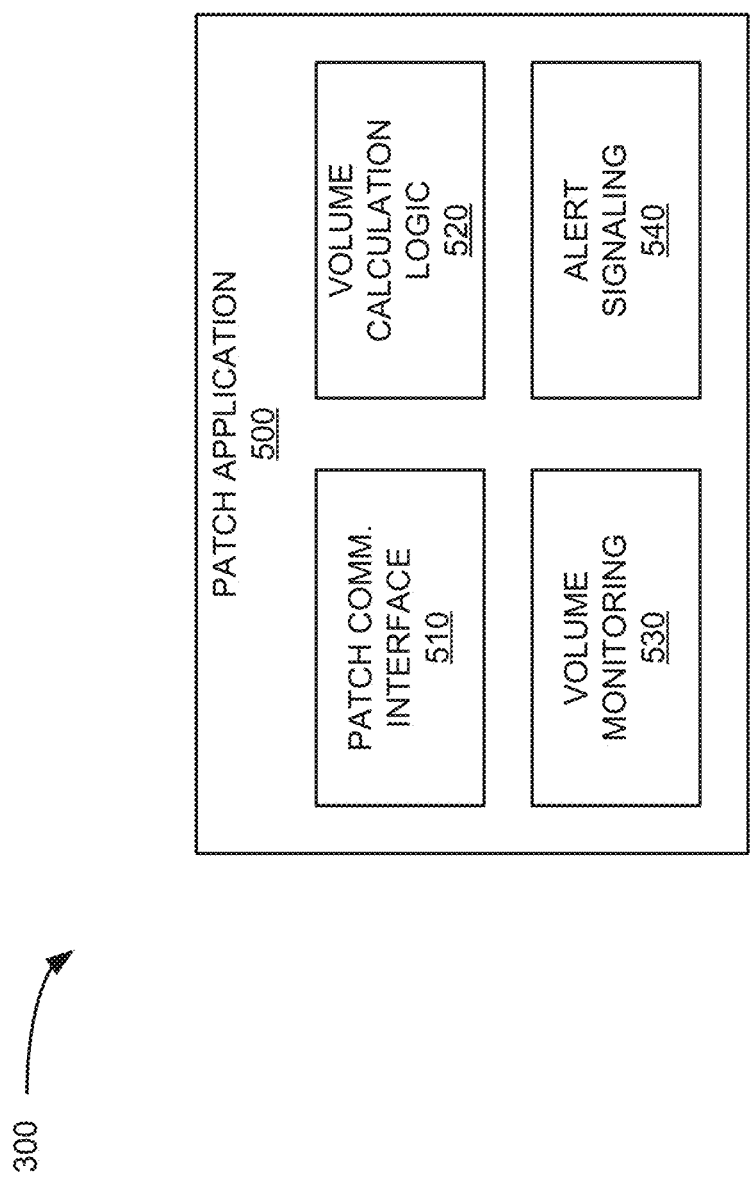
FIG. 5 is a block diagram of exemplary functional logic components implemented in the notification device of FIG. 1.

FIG. 5 is a block diagram of functional logic components implemented in notification device 300, in accordance with an exemplary implementation. Referring to FIG. 5, notification device 300 includes a patch application 500 with a patch communication interface 510, volume calculation logic 520, volume monitoring logic 530, and alert signaling logic 540.

Patch application 500 may provide a user interface (e.g. a graphical user interface) to request, receive, and/or present bladder volume sensing data from patch 200. Patch application 500 may allow a user to configure parameters for notification types, frequency, and/or timings. In one implementation, patch application 500 may be a proprietary application corresponding to a particular type of patch 200 and/or scanning system 100.

Patch communication interface 510 may establish communications between notification device 300 and patch 200 to enable periodic reporting of bladder volume data, on-demand requests for bladder volume, and/or alarm indication from patch 200.

Volume calculation logic 520 may receive sensor data from patch 200 and calculate a bladder volume corresponding to the sensor readings (e.g., from ultrasound transducers 460). For example, if patch 200 provides raw sensor data, volume calculation logic 520 may calculate bladder volume information based on signals received from patch 200. The calculated bladder volume information may include a quantitative bladder volume or a qualitative bladder volume based on bladder dimensions previously determined by scanning system 100 and communicated to notification device 300 as patch customization instructions 240.

Volume monitoring logic 530 may provide periodic or on-demand requests for sensor data from patch 200 and present bladder volume levels (e.g., via a display, speaker, or another output device of notification device 300). For example, volume monitoring logic 530 may obtain bladder volume readings from patch 200 or volume calculation logic 520. In one implementation, volume monitoring logic may present bladder volume readings in relation to a quantitative threshold (e.g., a reported number of milliliters compared to a maximum number of milliliters) or a qualitative threshold (medium, high, etc.).

Alert signaling logic 540 may include logic to determine if an alert signal (e.g., for a full or nearly full bladder) should be issued based on bladder volume readings from patch 200 or volume calculation logic 520 and present an alert/alarm, when necessary. In one implementation, alert signaling logic 540 may apply configurable parameters provided by a patient or caretaker. For example, a user (e.g., a patient, caretaker, or technician) may configure alert signaling logic to provide one or more of an audible (e.g., a tone or recording), visible (e.g., a message or light), or physical (e.g., vibration) alert signals. In another example, configurable parameters for alert signaling logic 540 may include different or multiple alert thresholds. In another implementation, alert signaling logic 540 may be configured to provide an alert signal based on detection of deficient patch conditions (e.g., patch displacement, poor contact, sensor failure, etc.).

Although FIG. 5 shows exemplary logical components of notification device 300, in other implementations, notification device 300 may include fewer logical components, different logical components, or additional logical components than depicted in FIG. 5. For example, in another implementation, notification device 300 may include a different form factor, such as a hearing aid, or pendant that does not include all the logical components shown in FIG. 5.

Figure 6:
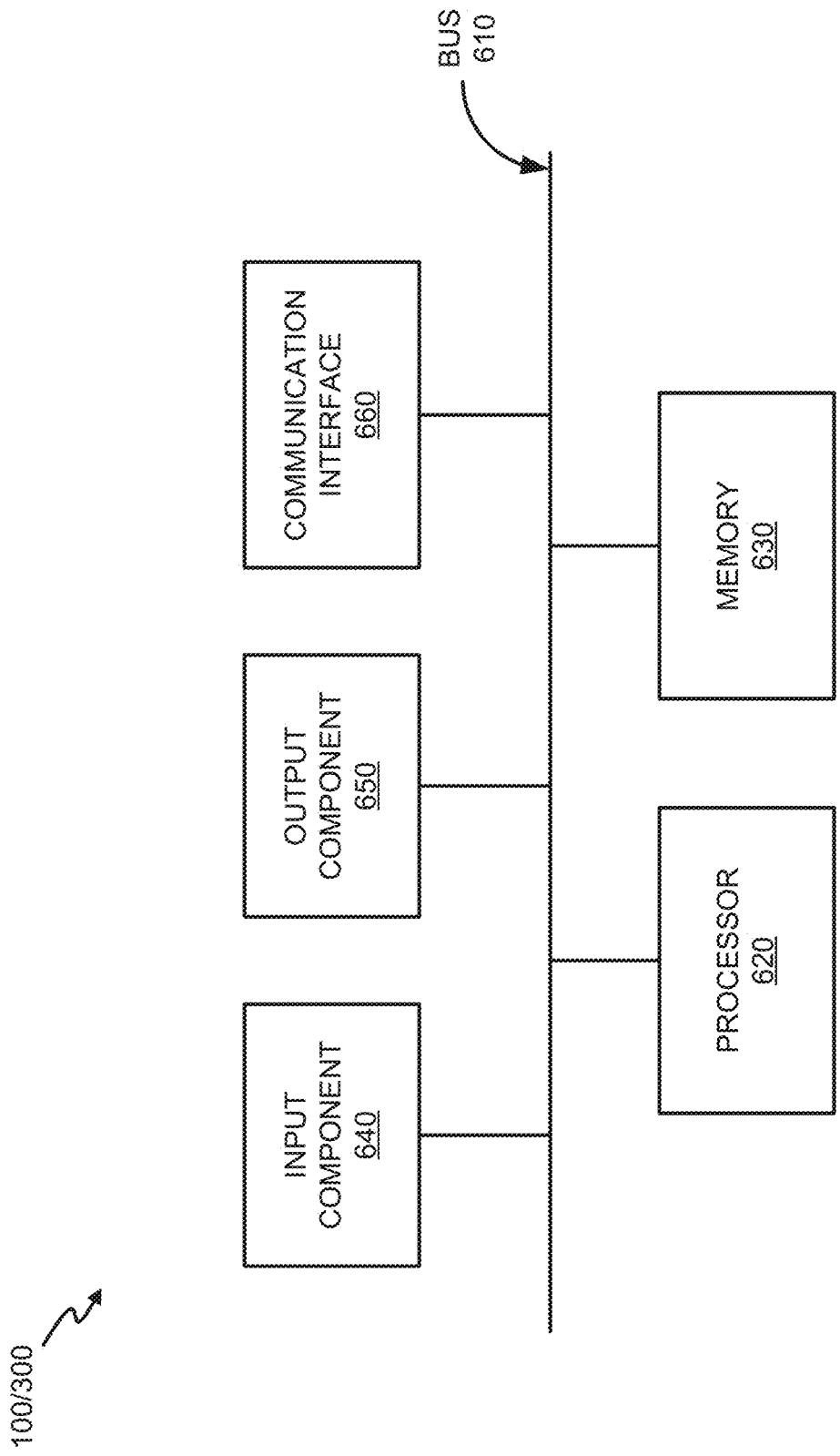
FIG. 6 is a block diagram illustrating exemplary components of a device that may correspond to one or more of the devices of the bladder monitoring system of FIG. 1.

FIG. 6 is a diagram illustrating exemplary components of a device 600. Device 600 may correspond, for example, to a component of scanning system 100 and notification device 300. Alternatively or additionally, scanning system 100 and notification device 300 may include one or more devices 600 and/or one or more components of device 600.

Device 600 may include a bus 610, a processor 620, a memory 630, an input component 640, an output component 650, and a communication interface 660. Although FIG. 6 shows exemplary components of device 600, in other implementations, device 600 may contain fewer components, additional components, different components, or differently arranged components than those depicted in FIG. 6. For example, device 600 may include one or more switch fabrics instead of, or in addition to, bus 610. Additionally, or alternatively, one or more components of device 600 may perform one or more tasks described as being performed by one or more other components of device 600.

Bus 610 may include a path that permits communication among the components of device 600. Processor 620 may include a processor, a microprocessor, or processing logic that may interpret and execute instructions. Memory 630 may include any type of dynamic storage device that may store information and instructions, for execution by processor 620, and/or any type of non-volatile storage device that may store information for use by processor 620. Input component 640 may include a mechanism that permits a user to input information to device 600, such as a keyboard, a keypad, a button, a switch, etc. Output component 650 may include a mechanism that outputs information to the user, such as a display, a speaker, one or more LEDs, etc.

Communication interface 660 may include a transceiver that enables device 600 to communicate with other devices and/or systems via wireless communications, wired communications, or a combination of wireless and wired communications. For example, communication interface 660 may include mechanisms for communicating with another device or system via a network. Communication interface 660 may include an antenna assembly for transmission and/or reception of RF signals. For example, communication interface 660 may include one or more antennas to transmit and/or receive RF signals over the air. Alternatively or additionally, communication interface 660 may be a logical component that includes input and output ports, input and output systems, and/or other input and output components that facilitate the transmission of data to other devices.

Device 600 may perform certain operations in response to processor 620 executing software instructions contained in a computer-readable medium, such as memory 630. A computer-readable medium may be defined as a non-transitory memory device. A memory device may include space within a single physical memory device or spread across multiple physical memory devices. The software instructions may be read into memory 630 from another computer-readable medium or from another device. The software instructions contained in memory 630 may cause processor 620 to perform processes described herein. Alternatively, hard-wired circuitry may be used in place of or in combination with software instructions to implement processes described herein. Thus, implementations described herein are not limited to any specific combination of hardware circuitry and software.

Device 600 may include fewer components, additional components, different components, and/or differently arranged components than those illustrated in FIG. 6. Additionally, or alternatively, one or more operations described as being performed by a particular component of device 600 may be performed by one or more other components, in addition to or instead of the particular component of device 600.

Figure 7:
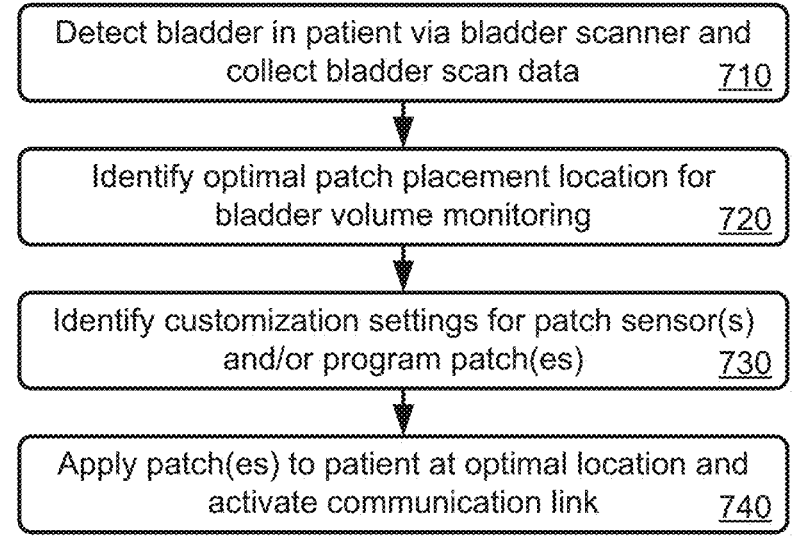
FIG. 7 is a diagram illustrating bladder monitoring patch application and customization procedures, according to an implementation described herein.

FIG. 7 is a diagram illustrating bladder monitoring patch application and customization procedures, according to implementations described herein. In particular, FIG. 7 illustrates a process 700 for using bladder monitoring system 10 with a programmable patch 200. Process blocks of FIG. 7A are described in conjunction with FIGS. 8A-9B, which include simplified schematics corresponding to certain process blocks of process 700.

Figure 8A:
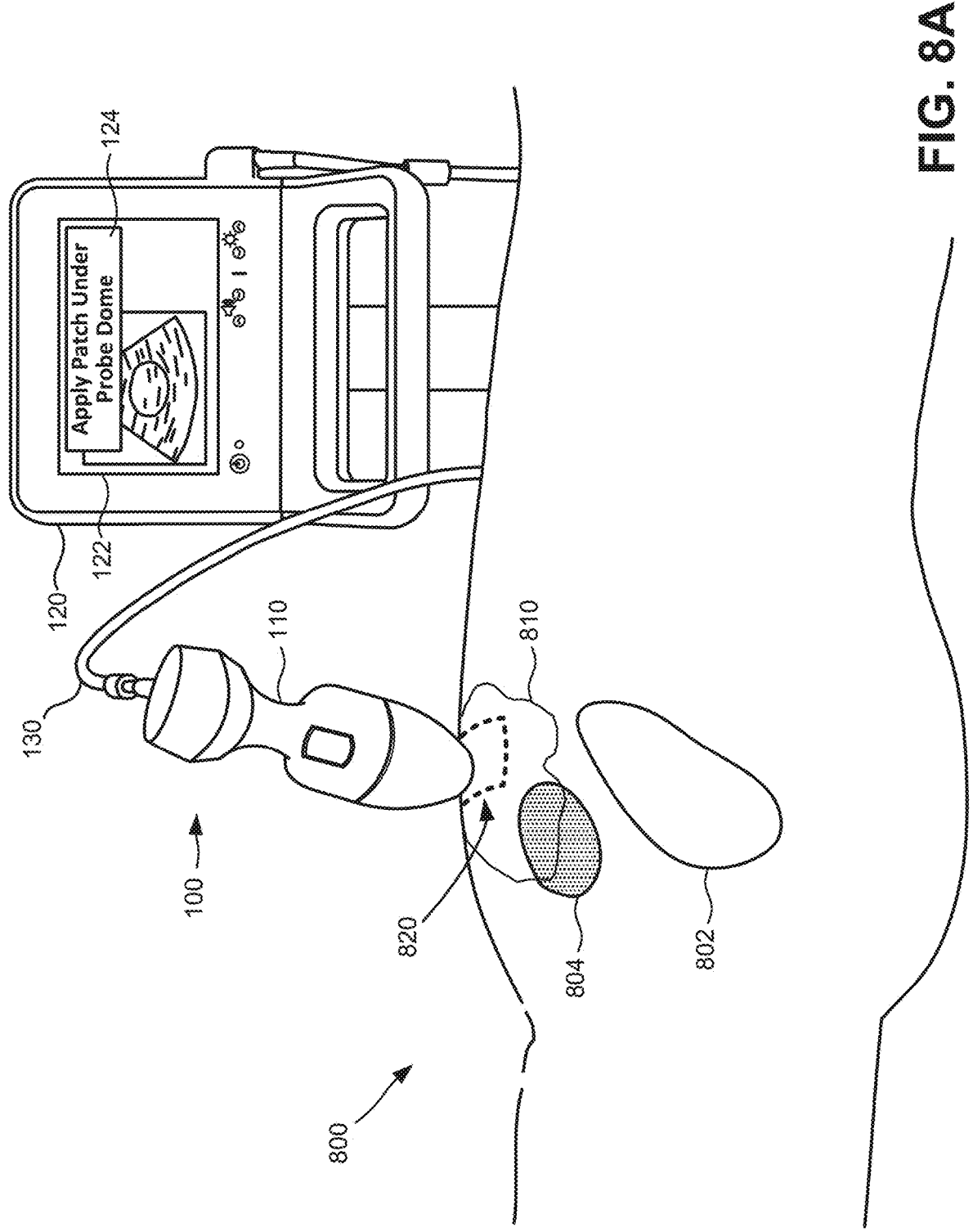

Referring to FIG. 7, process 700 may include using a bladder scanner to detect a bladder in a patient via a bladder scanner and collecting bladder scan data (block 710). For example, as shown in FIG. 8A, an acoustic gel or gel pads, illustrated at area 810 in FIG. 8A, may be applied to patient's skin over a region of interest (ROI) to provide an acoustical impedance match when a dome of probe 110 is placed against a patient's skin. In some implementations, display 122 may include a graphical user interface (GUI) that allows the user to select various features associated with an ultrasound scan. For example, display 122 may allow a user to select whether patient 150 is male, female or a child. This allows scanning system 100 to automatically adapt the transmission, reception, and processing of ultrasound signals to the anatomy of a selected patient, such as adapting system 100 to accommodate various anatomical details of male and female patients. In other implementations, system 100 may receive other types of patient features, such as body-mass index, age, etc., to further accommodate various anatomical details of the patient.

Base unit 120 may receive B-mode ultrasound images from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, a scan conversion can also be applied to make the bladder shape appear closer to the actual shape when presented on a display 122 of base unit 120.

Process 700 may further include identifying an optimal patch placement location for bladder volume monitoring (block 720). For example, scanning system 110 or a technician may select a patch 200 from a group of patch types with different pre-configured sensor settings (e.g., sized for child, male body, female body, small body-type, medium body-type, large body-type, different body mass indexes, etc.). Based on the B-mode ultrasound images and/or 3D renderings generated therefrom, scanning system 100 may identify an optimal placement location 820 for patch 200. Optimal placement location 820 may correspond to a location on the patient where sensors of patch 200 will most likely have an unobstructed view of bladder 802 without interference from pubic bone 804 or other obstructions. In one implementation, scanning system 100 may account for patch characteristics (e.g., patch dimensions, number of sensors, sensor types, sensor arrangement on patch, etc.) in determining placement location 820. For example, scanning system 100 may request a user to input a patch model number or particular patch information that may be used to cross-reference patch characteristics (e.g., stored in patch placement logic 330). In one implementation, scanning system 100 may guide a technician to position probe 110 over placement location 820, so that placement location 820 can be marked (e.g., with a sticker, pen, marker, stencil, etc.) by the technician. Placement location 820 may be indicated to a technician by text (e.g. text 124) on screen 122, an audible tone, or another indication, when probe 110 is positioned over placement location 820. In another implementation, scanning system 100 may guide a technician to position probe 110 over two or more different placement locations for use of multiple patches 200.

Figure 9B:
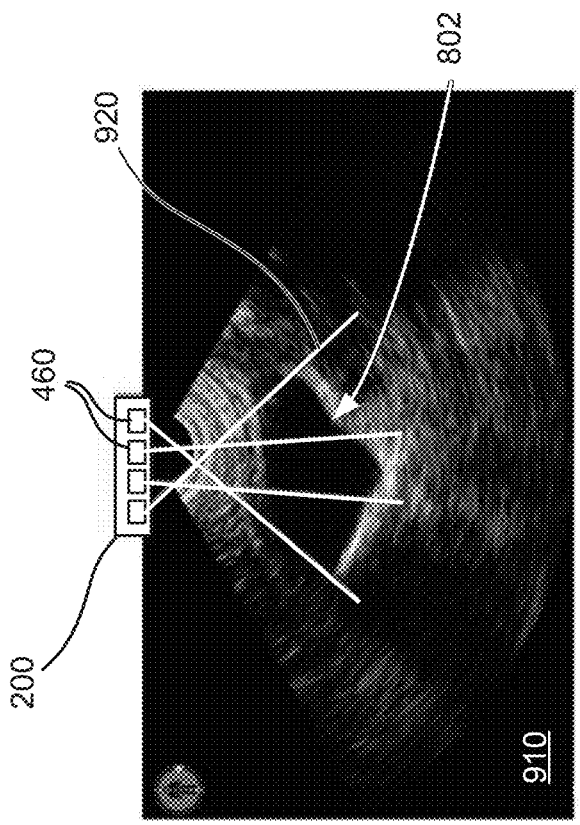
FIGS. 9A and 9B are simplified schematics of patch characteristics overlaid on a bladder scan image.
Figure 9A:
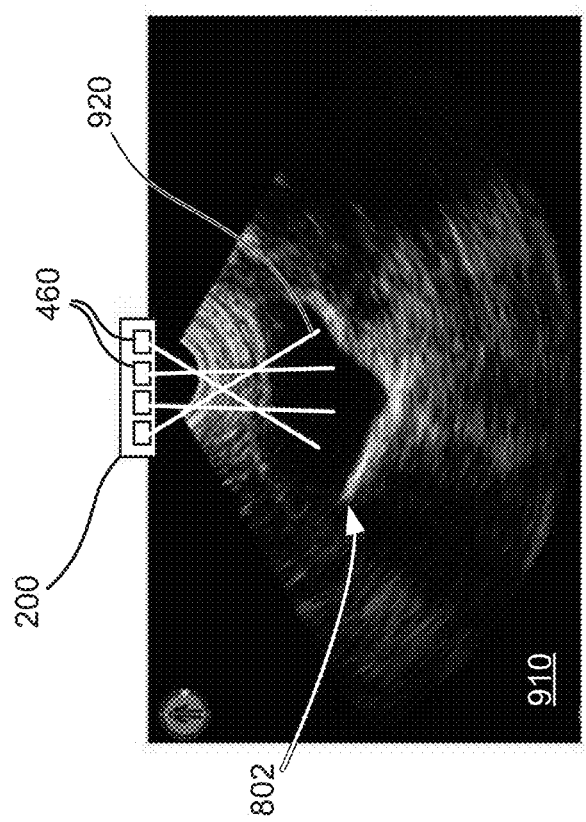

Process 700 may further include identifying customization settings for patch sensor(s) and/or programing the patch (block 730). For example, FIGS. 9A and 9B provide a simplified schematic of patch 200 characteristics overlaid on a bladder scan image 910. FIG. 9A represents initial settings for patch 200, where the predicted penetration depth and steering angles of signals 920 from sensors (e.g., ultrasound transducers 460) are not sufficient to cover the region of bladder 802. As shown in FIG. 9B, scanning system 100 may provide guidance, based on image 910, to increase penetration depth and widen the steering angles for predicted signals 920 from sensors (e.g., ultrasound transducers 460), so that patch 200 can provide adequate coverage of bladder 802. The guidance may be saved as modifications to the default patch settings and programmed into patch 200 to provide customization settings for patch 200 for the particular patient. Additionally, or alternatively, scanning system 100 may provide guidance, based on image 910, to select a different patch 200 with different pre-configured sensor settings (e.g., sized for small body-type, medium body-type, large body-type, different body mass indexes, etc.) to provide adequate coverage of bladder 802.

Figure 8B:
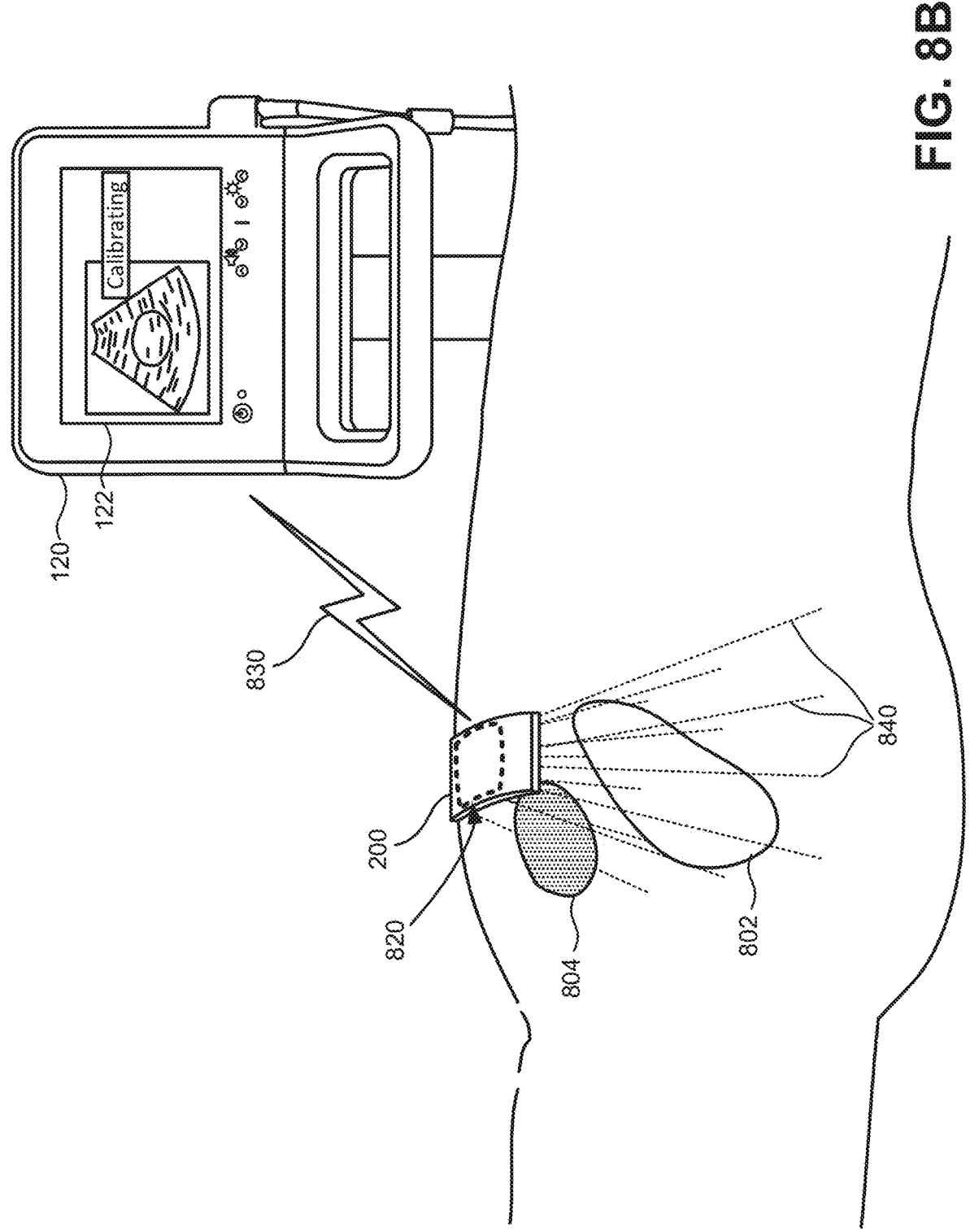

Process 700 may also include applying the one or more patches to the patient and activating a communication link (block 740). For example, as shown in FIG. 8B, a technician may apply patch 200 to placement location 820. The technician may power on patch 200, and scanning system 100 and patch 200 may form a wireless connection 830 (e.g., via a Bluetooth® pairing sequence, etc.). Alternatively, patch 200 and scanning system 100 may be connected via physical link (e.g. a USB cable). Patch 200 may initiate sensors (e.g., ultrasound transducers 460) to provide sensor readings to scanning system 100 for further verification/customization. Additionally, or alternatively, as shown in FIG. 8C, patch 200 and notification device 300 (e.g., patch communication interface 510) may form a wireless connection 850 (e.g., via a Bluetooth® pairing sequence, etc.). Wireless connection 850 may enable patch 200 to provide reference signals, periodic reporting of bladder volume data, on-demand requests for bladder volume, and/or alarm indication from patch 200. Alternatively, notification device 300 may be integral within patch 200.

Figure 10:
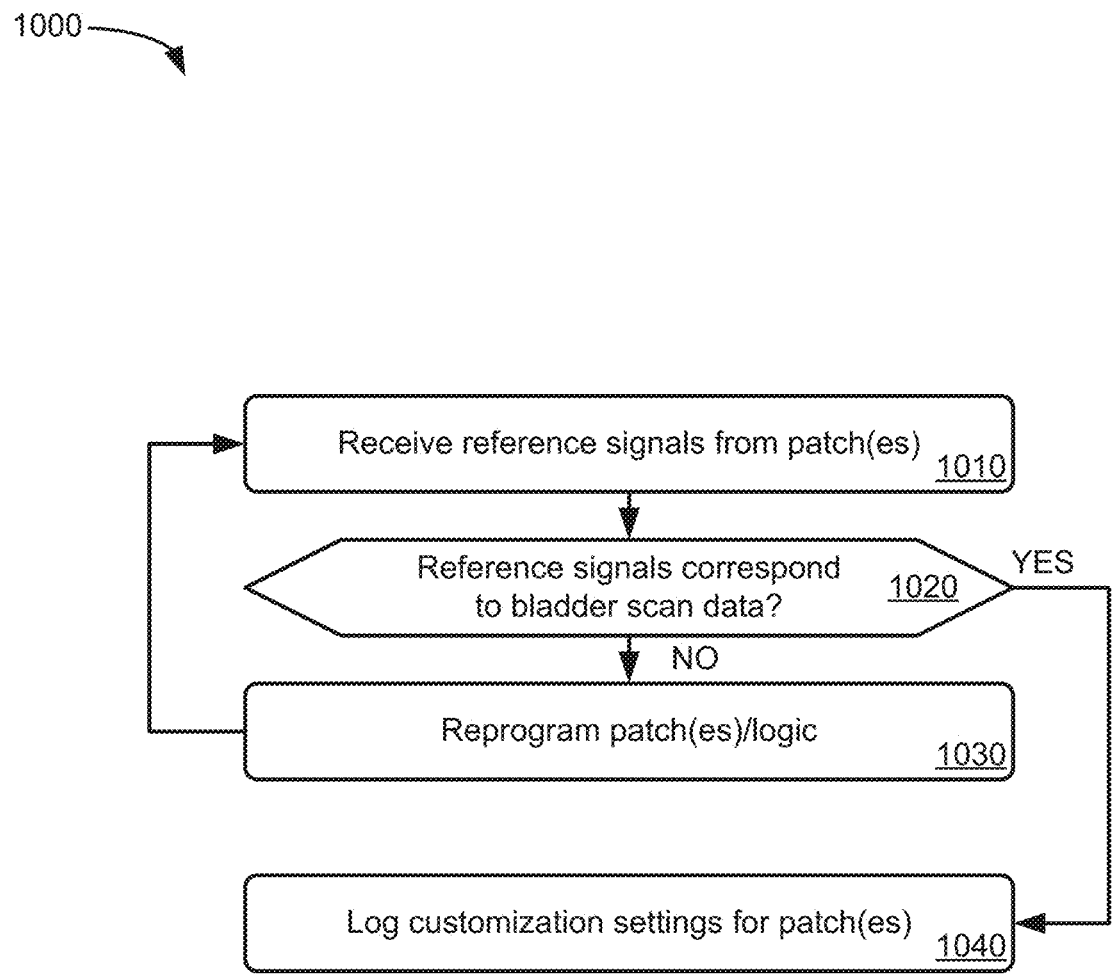
FIG. 10 is a diagram illustrating bladder monitoring patch application and customization procedures, according to another implementation described herein.

FIG. 10 is a diagram illustrating additional patch customization procedures, according to implementations described herein. Referring to FIG. 10, process 1000 may include receiving reference signal from an applied monitoring patch (block 1010) and determining if reference signals correspond to bladder scan data (block 1020). For example, patch 200 may establish a communication link with scanning system 100 and or notification device 300 to send reference signals (e.g., sensor readings from ultrasound transducers 460 or other sensors). In one implementation, scanning system 100 may correlate individual sensor readings with bladder scan data (e.g., collected by probe 110). In one implementation, scanning system 100 (e.g., patch correlation logic 344) may apply measured bladder characteristics from bladder characteristics unit 320 to correlate sensor echo signals (e.g., signals 840, FIG. 8B) of patch 200 to particular areas and projected volumes of the patient's bladder 802. In another implementation, notification device 300 may correlate individual sensor readings with bladder scan data.

If the reference signals do not correspond to the bladder scan data (block 1020-NO), process 1000 may include reprogramming one or more patches or processing logic (block 1030). For example, scanning system 100 may receive sensor signals from patch 200 and validate the sensor signals against bladder scan data from probe 110. In one implementation, sensor signals may be provided for different bladder conditions (e.g., pre-voiding, partial-voiding, post-voiding, etc.). Scanning system 100 may provide updated customization settings (e.g., to adjust intensity levels, steering directions, etc.,) that can be automatically or manually programmed into patch 200. Additionally, or alternatively, scanning system 100 may correlate individual sensor readings from patch 200 with bladder scan data (e.g., collected by probe 110). In one implementation, scanning system 100 (e.g., patch correlation logic 344) may apply measured bladder characteristics from bladder characteristics unit 320 to correlate sensor echo signals 840 (FIG. 8B) of patch 200 to particular areas and projected volumes of the patient's bladder 802. Scanning system 100 may provide the correlations, for example, to patch application 500 on notification device 300. In another implementation, scanning system 100 may provide instructions for adjusting a patch 200 position on the patient and/or replacing patch 200 with another patch having different pre-configured settings. Process 1000 may then return to process block 1010 to provide more signals for validation.

If the reference signals correspond to the bladder scan data (block 1020-YES), process 1000 may include logging the customization settings for the patches (block 1040). For example, particular application locations/positions, intensity levels, steering angles, sizes, etc. for patch 200 on the specific patient may be recorded. In one implementation, the customization settings may be managed similar to a medical equipment prescription, where a set of disposable patches 200 with the customization settings may be pre-configured for application and use outside a medical facility.

After confirming the reference signals correspond to the bladder scan data, patch 200 may report sensor results (e.g., monitoring signals 250) that indicate a bladder volume level (e.g., a quantitative or qualitative value) to notification device 300. Notification device 300 (e.g., alert signaling logic 540) may receive the bladder volume signals and present one or more of an audible, visible, or physical alert indicator. For example, as shown in FIG. 8C, notification device 300 may include an audible or visible indicator 860. The indicator 860 may include an approximate volume level (e.g., "BV over 75%" as shown in FIG. 8C) or a recommended action based on an estimated volume level (e.g., "discharge within 20 minutes").

Alternatively, as shown in FIG. 11, notification device 300 may include a dedicated or multi-feature device (e.g., a hearing aid, an activity monitor, fitness tracker, medical alert pendant, etc.) for providing an audible signal or instructions to a patient. In still other implementations, patch 200 (e.g., display/output unit 480) may present an alert indication.

Systems and methods described herein apply bladder scan information to improve placement and customization of monitoring patches. A bladder monitoring system may include a scanning system and a wearable bladder monitoring device (or patch). The scanning system may obtain scan data that shows a bladder in a patient and identifies, based on the scan data, a placement location on the patient for the wearable bladder monitoring device. The scanning system may indicate the placement location to a user; and identifies customization settings for one or more sensors of the wearable bladder monitoring device to enable the one or more sensors to detect extents of the bladder when the wearable bladder monitoring device is attached at the placement location.

Communication between the bladder scan system and monitoring patch simplifies customization over conventional wearable monitoring systems and improves precision of the monitoring patch. For example, customization of conventional systems may include taking discharge volume measurements (e.g., voiding the patient's bladder) after a patch is applied on the patient. It may take several (e.g., 10 or more) iterations of voiding until the patch can be finally tuned with the best configuration. By contrast, implementations described herein may use bladder scan technology to customize a patch for patient bladder monitoring at the time the patch is applied with minimal or no post-application tuning.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A bladder monitoring system, comprising:
a scanning system including an ultrasound probe, a base unit, and a first communication interface; and
a monitoring patch including one or more sensors to detect fluid in a bladder of a patient and a second communication interface to communicate with at least one of the scanning system or a notification device, wherein the monitoring patch includes a wearable device configured to be attached to the patient,
wherein the scanning system is configured to:
identify the bladder using scan data from the ultrasound probe,
indicate to a user, based on the scan data, a location on the patient where the monitoring patch should be attached, and
identify customization settings for the one or more sensors to enable the one or more sensors to detect extents of the bladder when the patch is attached at the location on the patient.

2. The bladder monitoring system of claim 1, wherein the scanning system is further configured to:
receive, via the first communication interface and after the monitoring patch is attached to the patient, reference signals from monitoring patch, and
provide, to the monitoring patch via the first communication interface, customization instructions for the one or more sensors, wherein the customization instructions are based on the reference signals and the scan data.

3. The bladder monitoring system of claim 2, wherein the customization instructions include instructions for:
associating particular combinations of readings from the one or more sensors with corresponding bladder volume levels.

4. The bladder monitoring system of claim 1, wherein the customization settings include:
a carrier frequency for the one or more sensors,
an acoustic intensity for the one or more sensors,
a steering angle for the one or more sensors,
a pulse repeating frequency for the one or more sensors,
signal bias for the one or more sensors,
gain level for the one or more sensors, or
a pre-processing method.

5. The bladder monitoring system of claim 1, wherein the one or more sensors include:

an ultrasound sensor,
a bio-impedance sensor,
a bio-reactance sensor,
a radio frequency sensor, or
an infrared sensor.

6. The bladder monitoring system of claim 2, further comprising:
the notification device including a third communication interface to receive monitoring signals from the monitoring patch,
wherein the monitoring patch is further configured to:
send, after receiving the customization instructions, the monitoring signals to the notification device, wherein the monitoring signals indicate a current volume of the bladder.

7. The bladder monitoring system of claim 6, wherein the monitoring signals from the monitoring patch include raw signals from the one or more sensors.

8. The bladder monitoring system of claim 6, wherein the monitoring signals from the monitoring patch include signals indicating a customized volume measurement of the bladder.

9. The bladder monitoring system of claim 1, wherein the scanning system is configured to: receive patch description information, and wherein indicating the location on the patient where the monitoring patch should be attached is further based on the patch description information.

10. The bladder monitoring system of claim 1, wherein the first communication interface includes a short-range wireless interface.

11. A bladder monitoring system, comprising:
a monitoring patch including one or more sensors to detect fluid in a bladder of a patient and a first communication interface to communicate with a notification device, wherein the monitoring patch includes a wearable device configured to be attached to the patient; and
the notification device including a second communication interface to receive monitoring signals from the monitoring patch, a third communication interface to communicate with a scanning system, and a processor configured to:
receive, via the third communication interface, bladder scan data from the scanning system,
receive, via the second communication interface and when the monitoring patch is attached to the patient, the monitoring signals from monitoring patch, and
determine, based on the bladder scan data and the monitoring signals, a fluid level in the bladder.

12. The bladder monitoring system of claim 11, wherein the notification device is further configured to:
indicate to a user, based on the scan data, a location on the patient where the monitoring patch should be attached.

13. A wearable bladder monitoring device, comprising:
one or more sensors, wherein the one or more sensors are pre-configured to detect fluid in a bladder of a patient;
a communication interface to receive customization settings for the one or more sensors, wherein the customization settings correspond to extents of a bladder of the patient, as measured by a bladder scanning system; and
a processor to implement the customization settings to adjust the one or more sensors, based on the customization settings, to detect extents of the bladder when the wearable bladder monitoring device is attached at a location on the patient.

14. The wearable bladder monitoring device of claim 13, wherein the one or more sensors include:
an ultrasound sensor,
a bio-impedance sensor,
a bio-reactance sensor,
a radio frequency sensor,
an infrared sensor,
an inertial measurement unit,
a temperature sensor, or
a humidity sensor.

15. The wearable bladder monitoring device of claim 13, further comprising:
another communication interface to send monitoring signals to a notification device, wherein processor is further to:
receive, from the one or more sensors, sensor readings that indicate a current volume of the bladder, and
send, via the other communication interface, the monitoring signals based on the sensor readings to the notification device.

16. The wearable bladder monitoring device of claim 13, wherein the customization settings include:
a carrier frequency for the one or more sensors,
an acoustic intensity for the one or more sensors,
a steering angle for the one or more sensors, or
a pulse repeating frequency for the one or more sensors.

17. The wearable bladder monitoring device of claim 13, wherein the one or more sensors are pre-configured to detect fluid in the bladder of one of:
a child,
a male body, or
a female body.

18. A bladder monitoring system, comprising:
a scanning system including an ultrasound probe, a processor, and a first communication interface; and
wherein the scanning system is configured to:
obtain, from a patient, bladder scan data using the ultrasound probe,
predict sensor signal characteristics, based on the bladder scan data, for a wearable monitoring patch to be applied to the patient, wherein the wearable monitoring patch includes one or more sensors to detect fluid in a bladder of the patient, and
indicate to a user, based on the predicting, a location on the patient where the monitoring patch should be attached.

19. The bladder monitoring system of claim 18, wherein the monitoring patch is pre-configured with customized settings for the one or more sensors, and wherein the scanning system is further configured to:
identify one type of wearable monitoring patch, from a group of pre-configured monitoring patches for different patient body types, that enable the wearable monitoring patch to detect extents of the bladder when the patch is attached at the location on the patient.

20. The bladder monitoring system of claim 18, wherein the scanning system is further configured to:
identify customization settings for the one or more sensors to enable the one or more sensors to detect extents of the bladder when the patch is attached at the location on the patient.

* * * * *